(12) United States Patent
Miyazaki et al.

(10) Patent No.: US 8,723,536 B2
(45) Date of Patent: May 13, 2014

(54) INSPECTION APPARATUS, SUBSTRATE MOUNTING DEVICE AND INSPECTION METHOD

(75) Inventors: Yusuke Miyazaki, Hitachinaka (JP); Kenji Aiko, Ninomiya (JP); Yuichiro Iijima, Hitachinaka (JP); Yuichiro Kato, Mito (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/580,473

(22) PCT Filed: Jan. 14, 2011

(86) PCT No.: PCT/JP2011/000161
§ 371 (c)(1), (2), (4) Date: Sep. 20, 2012

(87) PCT Pub. No.: WO2011/121868
PCT Pub. Date: Oct. 6, 2011

(65) Prior Publication Data
US 2013/0154675 A1    Jun. 20, 2013

(30) Foreign Application Priority Data
Mar. 31, 2010 (JP) ................. 2010-080071

(51) Int. Cl.
*G01R 31/00* (2006.01)
(52) U.S. Cl.
USPC .................................... 324/750.01

(58) Field of Classification Search
USPC ................. 324/750.01–750.3, 754.01–754.3, 324/762.01–762.1; 257/48; 438/14–18
See application file for complete search history.

(56) References Cited

U.S. PATENT DOCUMENTS

| 6,846,213 B2 * | 1/2005 | Sato .................................. 445/6 |
| 7,406,759 B2 * | 8/2008 | Yamamoto et al. ............. 29/559 |
| 7,607,647 B2 | 10/2009 | Zhao et al. |
| 2002/0014894 A1 * | 2/2002 | Yonezawa et al. ............ 324/760 |

FOREIGN PATENT DOCUMENTS

| JP | 4-357820 A | 12/1992 |
| JP | 5-291112 A | 11/1993 |
| JP | 11-111819 A | 4/1999 |
| JP | 2000-223388 A | 8/2000 |
| JP | 2001-267404 A | 9/2001 |
| JP | 2004-253756 A | 2/2004 |
| JP | 2006-324692 A | 11/2006 |
| JP | 2007-81450 A | 3/2007 |

* cited by examiner

Primary Examiner — Tung X Nguyen
(74) Attorney, Agent, or Firm — Mattingly & Malur, PC (57) ABSTRACT

Non-contact type displacement sensors which measure the height of a substrate surface are installed above the substrate in order to hold the upper surface of the substrate at a desired height or to maintain the flatness of the substrate. A substrate mounting device is such that a plurality of grooves and of barriers are provided on the upper surface of a table and air is supplied between the substrate and the table to enable the pressure of air to displace the substrate. In addition, the substrate mounting device has such a structure as to make it possible to deform the substrate into an arbitrary convex-concave shape or to make the substrate flat by feeding back the output of the displacement sensor.

17 Claims, 5 Drawing Sheets

INSPECTION APPARATUS, SUBSTRATE MOUNTING DEVICE AND INSPECTION METHOD

TECHNICAL FIELD

The present invention relates to an inspection apparatus and an inspection method. The present invention relates to a substrate holding device that is rotated integrally with a substrate while supporting, for example, an outer circumferential side of the substrate, and to a substrate inspection or processing apparatus using the substrate holding device.

BACKGROUND ART

In manufacturing processes for products such as semiconductor devices, thin display screens, magnetic disks and the like, substrates such as semiconductor wafers, glass substrates, disk substrates and the like are processed and the processed substrates are inspected. While being rotated, the substrate is processed and inspected in many cases. In surface inspection to determine whether or not a defect such as a flaw or the like or foreign matter exists on the front surface of a semiconductor wafer, while the semiconductor wafer is rotated, an area to be irradiated with inspection light is shifted in the radial direction of the semiconductor wafer. In this way, the inspection light spirally scans the front surface of the semiconductor wafer to detect a defect or foreign matter on the entire surface of the semiconductor wafer in a short time.

Along with miniaturization of a circuit pattern, a defect or foreign matter occurring even on the rear surface of a substrate tends to be controlled and reduced for products such as semiconductor devices, thin display screens, magnetic disks and the like. For this reason, the manufacturing process needs to process and inspect not only the front surface but the rear surface of the substrate in a non-contact state.

In view of the above, a substrate holding device is proposed that can rotate a substrate while being in non-contact with the front surface and rear surface of the substrate (for example, see Patent Documents 1 and 2).

PRIOR ART LITERATURE

Patent Documents

Patent Document 1: JP-2004-253756-A (paragraphs 0024 to 0039 and FIGS. 1 to 4)
Patent Document 2: U.S. Pat. No. 7,607,647 B2

SUMMARY OF THE INVENTION

Problems to be Solved by the Invention

Conventional substrate mounting apparatus are such that the rear surface of a wafer substrate comes into contact with a projecting pin, a rim or the like. As a result such a contact portion is contaminated. To prevent the rear surface of the wafer from being coming into contact with the projecting pin, the rim or the like, the side surface of the wafer substrate may be supported. In this case, however, the wafer substrate is sagged by the own weight thereof and thereby the flatness of the front surface of the substrate is impaired, which leads to an obstacle to various processes.

The present invention has been made in view of the above situation and aims to provide a substrate mounting apparatus that can hold a substrate without contact with the rear surface thereof while maintaining the flatness of the substrate.

Means for Solving the Problems

The present invention has the following characteristics. The present invention may have an independent one of the following characteristics or any combination thereof in some cases.

The first aspect of the present invention is characterized by controlling flatness of a substrate by controlling pressure on the rear surface side of the substrate.

The second aspect of the present invention is characterized in that concavity-convexity is formed on a portion opposed to the rear surface of the substrate, a medium is supplied to the portion and the supply amount of the medium is controlled.

The third aspect of the present invention is characterized by controlling the temperature of the medium.

The fourth aspect of the present invention is characterized in that concavity-convexity is formed on a portion opposed to the rear surface of the substrate and volume between the rear surface of the substrate and the concavity-convexity is controlled.

The fifth aspect of the present invention is characterized in that the flatness of the substrate is measured from the side where the substrate is inspected and the pressure is controlled based on a measurement result.

The sixth aspect of the present invention is characterized in that an inspection apparatus for inspecting a substrate includes a substrate mounting device and the substrate mounting device has a holding portion disposed on an outer circumferential portion of the substrate mounting device so as to mount the substrate thereon, a structure formed at a portion opposed to a rear surface of the substrate, and a first control section for controlling pressure between the rear surface of the substrate and the structure.

The seventh aspect of the present invention is characterized in that the substrate mounting device is a rear surface non-contact type substrate device.

The eighth aspect of the present invention is characterized in that the structure is concavity-convexity.

The ninth aspect of the present invention is characterized in that the structure is formed in a circle.

The tenth aspect of the present invention is characterized in that the structure is formed in a straight line.

The eleventh aspect of the present invention is characterized by including a first measuring section for measuring displacement of the substrate disposed on a side where the substrate is inspected, and in that the first control section controls pressure between the rear surface of the substrate and the structure on the basis of a measurement result of the first measuring section.

The twelfth aspect of the present invention is characterized by including a medium supply section for supplying a medium to a portion opposed to the rear surface of the substrate, and in that the first control section includes a second control section for controlling a supplied amount of the medium.

The thirteenth aspect of the present invention is characterized by including a second measuring section for measuring temperature of the medium; and a third control section for controlling the temperature of the medium on the basis of a measurement result of the second measuring section.

The fourteenth aspect of the present invention is characterized in that the medium is gas.

The fifteenth aspect of the present invention is characterized in that the first control section includes a fourth control section for controlling volume between the rear surface of the substrate and the structure.

The sixteenth aspect of the present invention is characterized in that the structure has a first piezo element, and the fourth control section includes a first drive section for driving the first piezo element.

The seventeenth aspect of the present invention is characterized in that the holding section includes a second piezo element, and the inspection apparatus includes a second drive section for driving the second piezo element.

The eighteenth aspect of the present invention is characterized in that a plurality of substrate holding portions installed at an outer circumferential portion of the substrate can independently be moved in a direction vertical to a substrate surface.

The nineteenth aspect of the present invention is characterized in that a rotating table located on the rear surface side of the substrate has a plurality of concentric barriers and a substrate holding device is provided that can control an interval between an upper surface of the barrier and the rear surface of the substrate.

The twentieth aspect of the present invention is characterized in that a rotating table located on the rear surface side of the substrate has a plurality of concentric barriers and a substrate holding device is provided that can control a concave portion between the corresponding barriers, i.e., an interval between a rotating table surface and the rear surface of the substrate.

The twenty-first aspect of the present invention is characterized in that a rotating table located on the rear surface side of the substrate has a plurality of concentric barriers and a substrate holding device is provided that allows gas to flow between the rotating table and the rear surface of the substrate and can control the flow rate of the gas.

The twenty-second aspect of the present invention is characterized by including a substrate holding device that can control the operation of the substrate holding portion on the basis of the flatness information of the substrate obtained by using one or more non-contact type displacement sensors.

The twenty-third aspect of the present invention is characterized by including a substrate holding device that can control an interval between an upper portion of a barrier on a rear surface side of a substrate and a rear surface of the substrate on the basis of flatness information of the substrate obtained by using one or more non-contact type displacement sensors.

The twenty-fourth aspect of the present invention is characterized by including a substrate holding device that can control an interval between a concave portion between corresponding barrier portions on the rear surface side of the substrate and a rear surface of the substrate of the substrate obtained by using one or more non-contact type displacement sensors.

The twenty-fifth aspect of the present invention is characterized by including a substrate holding device that can control a flow rate of gas allowed to flow between a rotating table on a rear surface side of a substrate and the rear surface of the substrate on the basis of flatness information of the substrate obtained by using one or more non-contact type displacement sensors.

Effects of the Invention

According to the present invention, the flatness of each substrate is made controllable; therefore, the substrate holding device can be provided that can ensure the flatness of a front surface of the substrate without contaminating the rear surface of the substrate. Further, an inspection or processing apparatus using the substrate holding mechanism can be provided.

BRIEF DESCRIPTION OF THE DRAWINGS

[FIG. 1]
[FIG. 4]
[FIG. 5]
[FIG. 6]
[FIG. 7]
[FIG. 8]
[FIG. 9]
[FIG. 10]

MODE FOR CARRYING OUT THE INVENTION

Embodiments of the present invention will next be described in detail with appropriate reference to the drawings. Incidentally, portions common to each other in the drawings are denoted with the same reference numerals and their explanations are omitted.

An inspection or processing apparatus according to an embodiment of the present invention inspects or processes products such as semiconductor devices, thin display screens, magnetic disks or the like in a process for manufacturing substrates such as semiconductor wafers, glass substrates, disk substrates or the like. A surface inspection apparatus or a particle counter is used as the inspection apparatus. The surface inspection apparatus determines the presence of a defect or foreign matter on a substrate while rotating the substrate. A drug solution processing apparatus or a spin coater is used as the processing apparatus. The drug solution processing apparatus performs drug solution processing, cleaning and drying while rotating the substrate. The spin coater coats, develops and peels resist. In the following description, a wafer is mainly assumed as the substrate and a surface inspection apparatus is mainly assumed as the inspection or processing apparatus.

Figure 1:
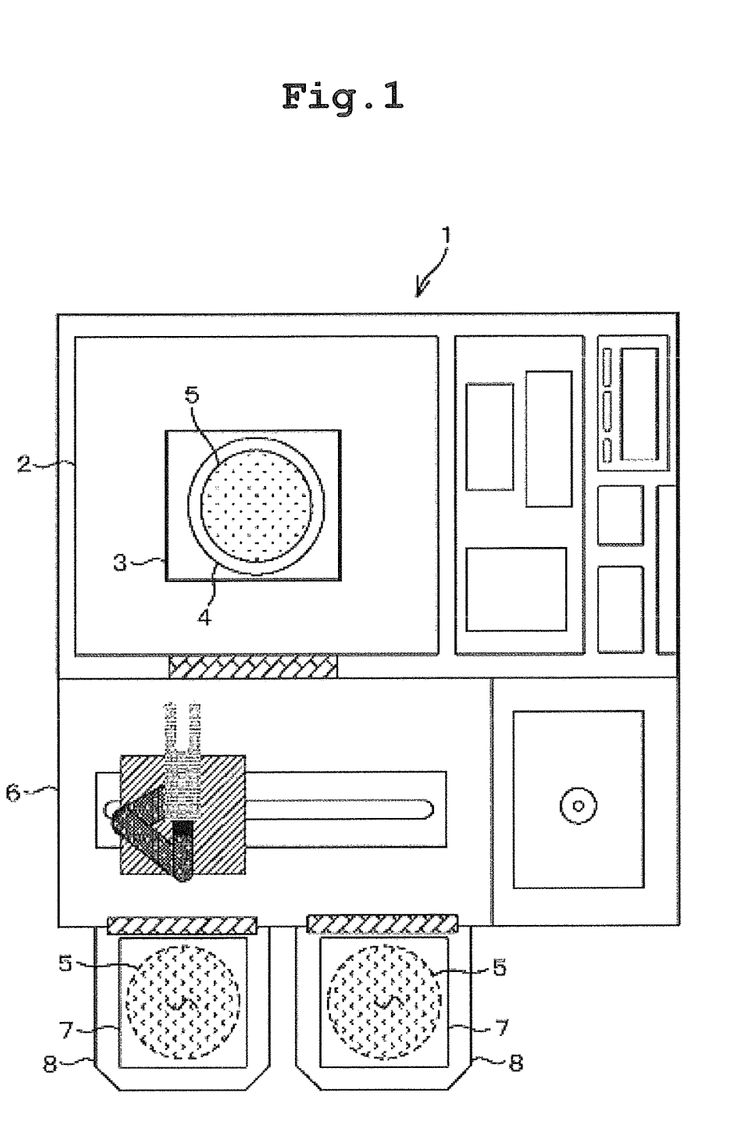
FIG. 1 is a top view showing a schematic configuration of a surface inspection apparatus.

As shown in FIG. 1, an inspection apparatus (a surface inspection apparatus) 1 according to the present embodiment of the invention includes an inspecting section 2 which directly inspects a substrate (hereinafter referred to as the wafer in the present embodiment) 5; a wafer transfer robot 6; and cassette tables 8. A cassette 7 storing a plurality of the wafers 5 is transferred to each of the cassette tables 8. The wafers 5 are housed in the cassette 7 at regular intervals in the depth direction of the drawing. Incidentally, if the inspection apparatus 1 is replaced with a processing apparatus, the inspecting section 2 is needed only to be replaced with a processing section.

The inspecting section 2 has a wafer holding device 3. The wafer holding device 3 has a rotatable rotating table 4. The wafer transfer robot 6 transfers a wafer 5 from the cassette 7 to the rotating table 4 and after the completion of inspection, transfers it from the rotating table 4 to the cassette 7.

A light-emitting system and a light-receiving system both not shown are arranged above the rotating table 4. The light-emitting system emits an optical beam such as laser light or the like to the front surface of the wafer 5 placed on the rotating table 4. While the wafer 5 is rotated by the rotating table 4, the wafer holding device 3 is linearly shifted in the radial direction of the wafer 5. In this way, the optical beam emitted from the light-emitting system spirally scans the front surface of the wafer 5. The light-receiving system detects light reflected or scattered from the front surface of the wafer 5. The detected signals of the light-receiving system are processed by an image signal processor not shown, whereby foreign matter existing on the front surface of the wafer 5 is detected.

The wafer holding device 3 that can ensure the flatness of the front surface of the wafer 5 is indispensable to stable detection of the foreign matter.

A description is below given of a method of controlling the flatness of the upper surface of a wafer.

A description is first given of a method of measuring the position of the upper surface of a wafer. Since the wafer 5 is rotated for inspection, a plurality of displacement-measuring sensors 11 are installed in the radial direction of the wafer. By rotating the wafer 5 for measurement, positional data of the entire surface of the wafer 5 can be obtained at predetermined radial pitches (intervals). The displacement-measuring sensors used in this case need to be in non-contact with the wafer, to be small in size for the installation at the predetermined pitches and to have such responsiveness as to be able to measure rotational speed at the predetermined intervals on the circumference of the wafer. For example, as regards the responsiveness, it is assumed that rotation speed is several thousand rpm, the data interval on the circumference is 10 mm, and the maximum measurement radius is 150 mm. In this case, circumferential velocity is from approximately $1.0 \times 10^4$ mm/sec to $5.0 \times 10^4$ mm/sec and thus the necessary frequency of the displacement-measuring sensor is several kHz.

Figure 2:
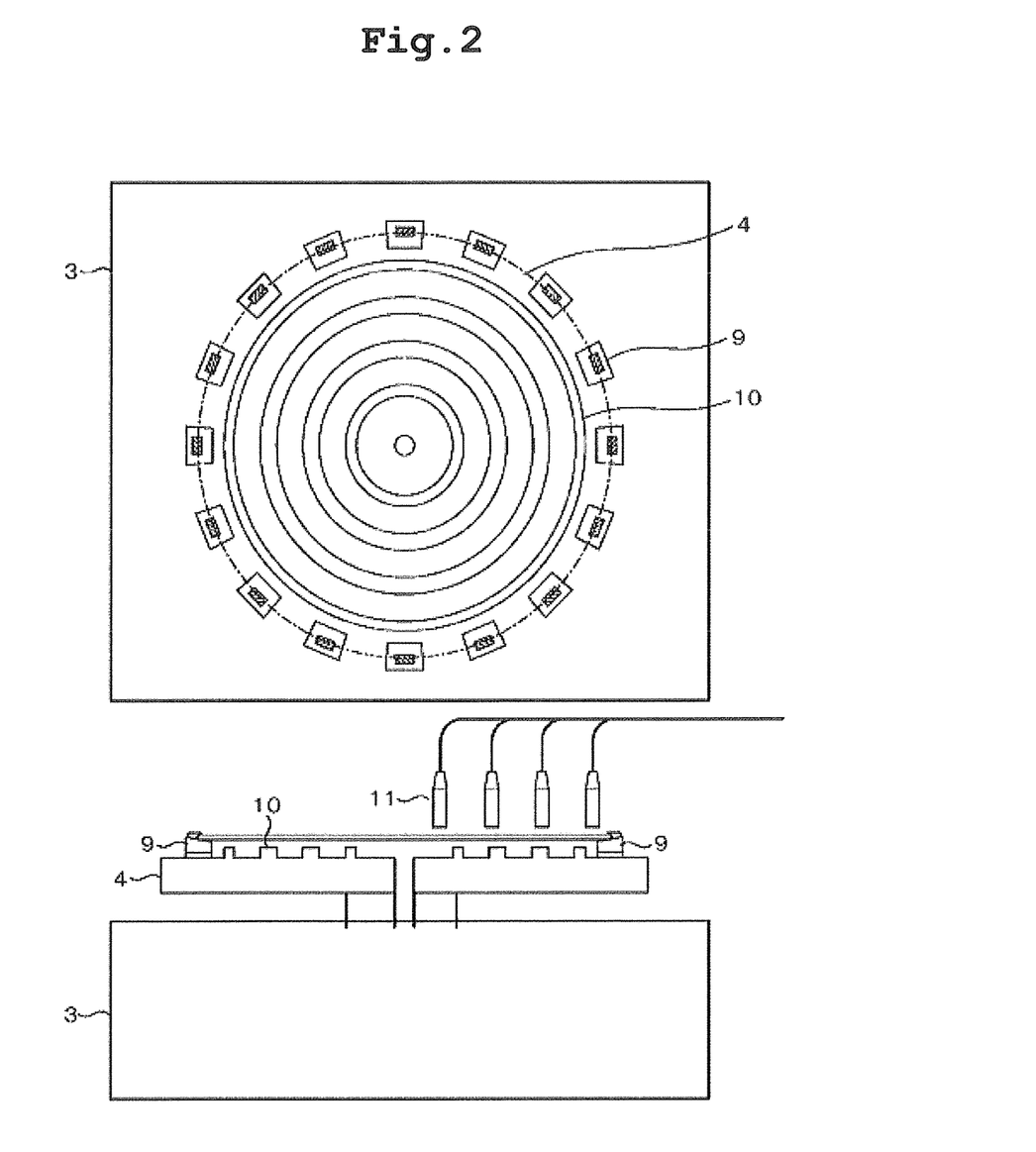
[FIG. 2]
FIG. 2 includes a front view and a top view schematically showing a wafer-holding device.

A state of mounting the displacement-measuring sensors is shown in FIG. 2. In this case, the displacement-measuring sensor 11 is e.g. a capacitance sensor. The capacitance sensor of a commercially available type has a responsiveness of 6 kHz to 15 kHz and a measurement resolution of 0.05 μm in the longitudinal direction of the capacitance sensor (the interval-direction with respect to the capacitance sensor). Thus, the capacitance sensor can satisfy conditions such as desired responsiveness, measurement accuracy, other mounting and the like.

Figure 3:
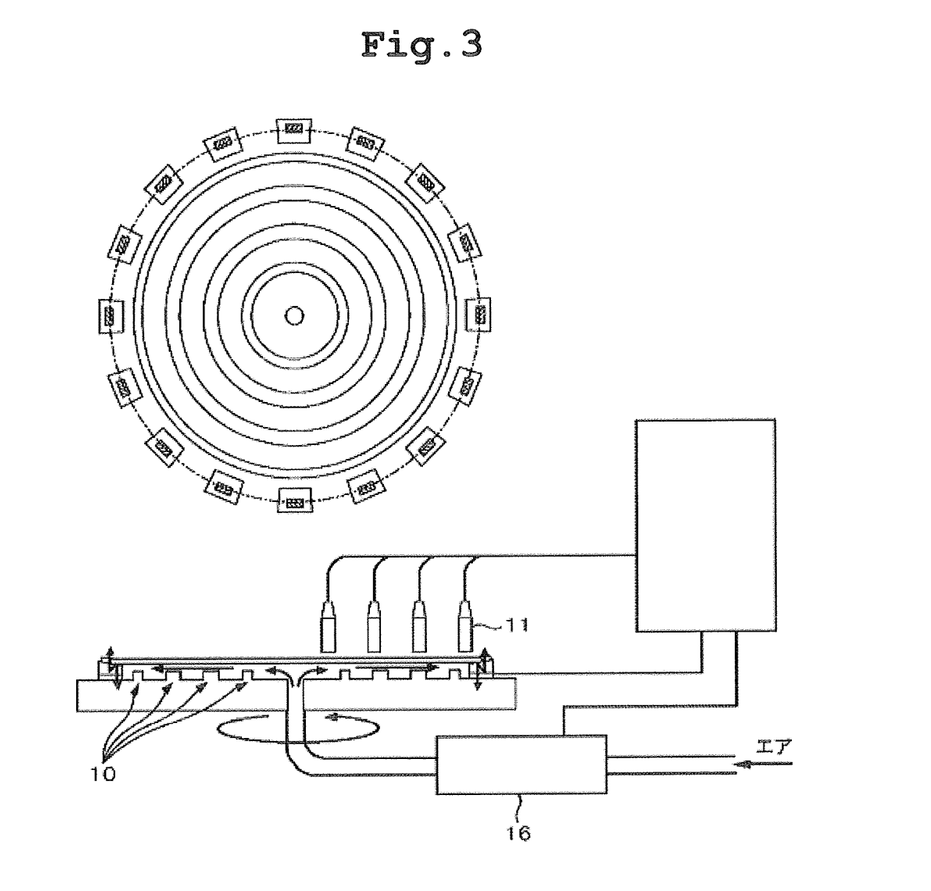
[FIG. 3]
FIG. 3 includes a front view and a top view schematically showing the wafer-holding device.

A method for raising and lowering the position of the upper surface of the wafer 5 is described below. A method for using the pressure of gas is exemplified in FIG. 3 as a means for changing the position of the wafer 5 from the rear surface thereof in a non-contact manner. The present embodiment uses air (e.g. fluid such as air or the like) as gas for explanation. A flow controller 16 shown in FIG. 3 is used to implement a method for controlling the pressure and flow of air to regulate force of pushing up the rear surface of the wafer 5. More specifically, air is supplied from the vicinity of the central axis of the wafer rotating table to the upper surface of the rotating table. The upper surface of the rotating table is provided with a plurality of concentric grooves with different radii. Barriers are each formed between the corresponding grooves.

Figure 4:
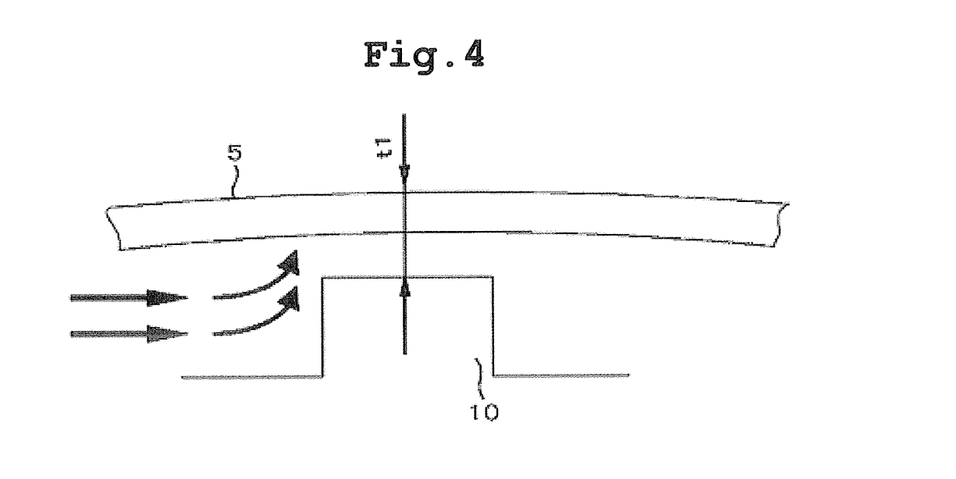
FIG. 4 shows sagging of a wafer resulting from an air pressure change due to barriers.

As shown in FIG. 4, the wafer 5 is placed on the rotating table. When flowing along a groove portion, the pressurized air flows through a narrow clearance t1 between a barrier portion and the wafer 5. Therefore, the air pressure is further increased to produce the force of pushing up the wafer 5. In other words, the wafer 5 is about to come into a convex state.

Figure 5:
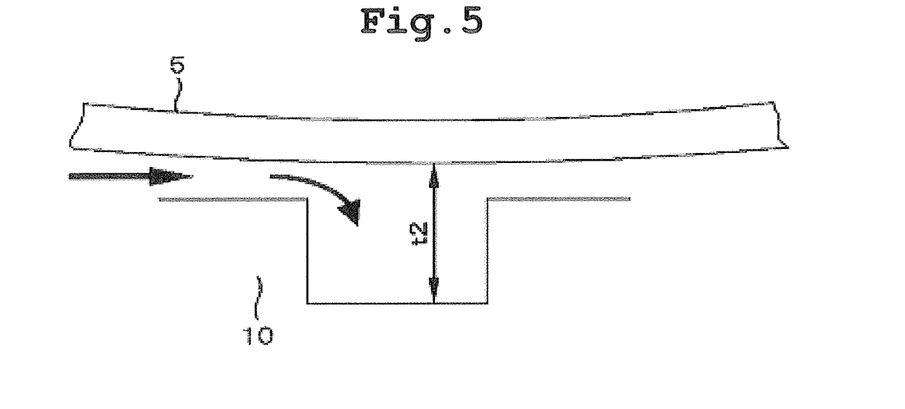
FIG. 5 shows sagging of the wafer resulting from an air pressure change due to a groove.

In contrast, as shown in FIG. 5, when the pressurized air flows along a groove portion, since the height of the space between the groove portion and the wafer 5 is t2, that is, since the volume of the space is increased, a portion between the wafer 5 and the rotating table 5 is reduced in pressure. At this time, the wafer 5 is about to come into a concave state due to the influence of the pressure. A plurality of the convexity-concavity forming structures are provided in the radial direction of the wafer; therefore, the convexity and concavity of the wafer 5 can be controlled in the radial direction.

Further, the convexity-concavity structures are arranged at predetermined intervals in the circumferential direction of the wafer; therefore, the convexity and concavity can be controlled on the entire surface of the wafer 5. The output of the displacement-measuring sensor described earlier is synchronized with the convexity-concavity structures. This makes it possible to control the convex or concave shape of the entire surface of the wafer 5. The entire surface of the wafer 5 can be controlled to have constant flatness if necessary.

Figure 6:
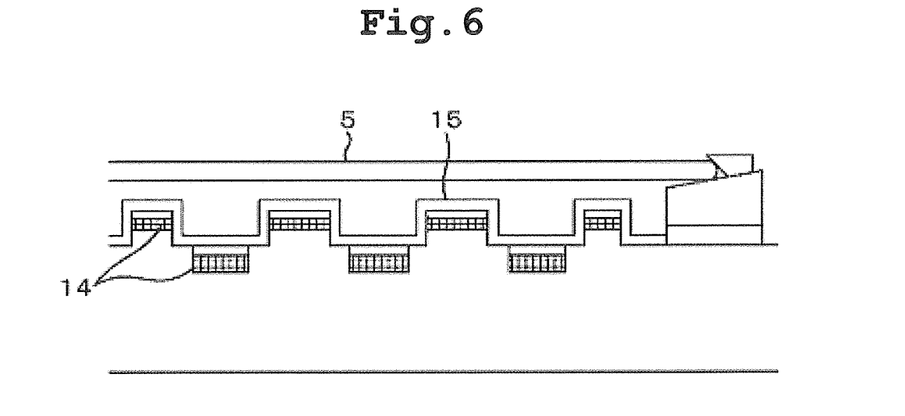
FIG. 6 shows means for changing the height of the barrier and of a groove portion by use of a piezo element.

A description is below given of another example of the means for changing the position of the wafer 5 from the rear surface in a non-contact manner by use of air. As shown in FIG. 6, the grooves and the barriers on both sides of a corresponding groove on the rotating table 4 are made to have the same shapes as those of the previous example. The previous example changes the pressure and flow of supplying air. However, this example makes pressure and flow constant and allows air to flow between the wafer 5 and the rotating table 4 from the vicinity of the center of the wafer 5 toward the outer circumference.

An increase in the upward force of air can be achieved by allowing a drive force such as a piezo element 14 to push up the upper surface of the barrier to narrow the clearance between the wafer 5 and the upper surface of the barrier. In this case, the pressure of air is increased with such narrowing. Along with the increased pressure of air, the wafer 5 is pushed upward to become convex.

In contrast, if the concave surface (the bottom surface) of the groove portion is pushed downward by the driving source such as a piezo element or the like, air pressure is reduced with the increased volume of the concave portion. Due to this pressure-reducing effect, the wafer 5 is made saggy (is shaped into concavity), that is, the wafer 5 has a concave shape. As with the previous example, this structure is provided at a plurality of positions in the radial and circumferential directions. This makes it possible to control the convexity and concavity of the wafer 5 over the entire surface of the wafer 5. Further, it is possible to control the entire surface of the wafer 5 into constant flatness.

Figure 7:
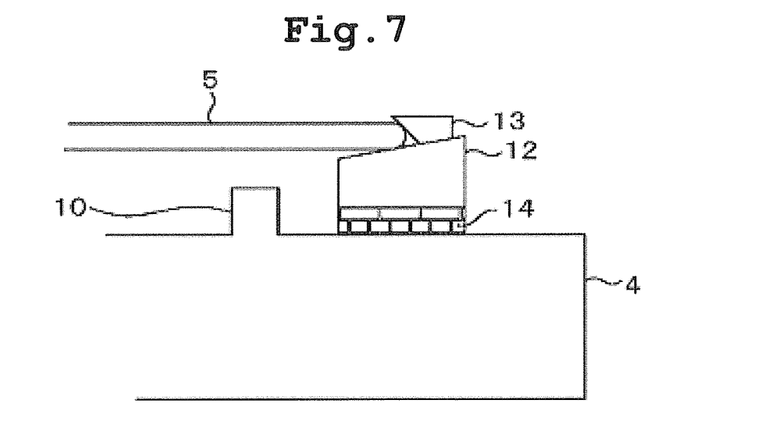
FIG. 7 shows means for changing the height of a wafer holding means by use of the piezo element (a state where the piezo element is contracted).
Figure 8:
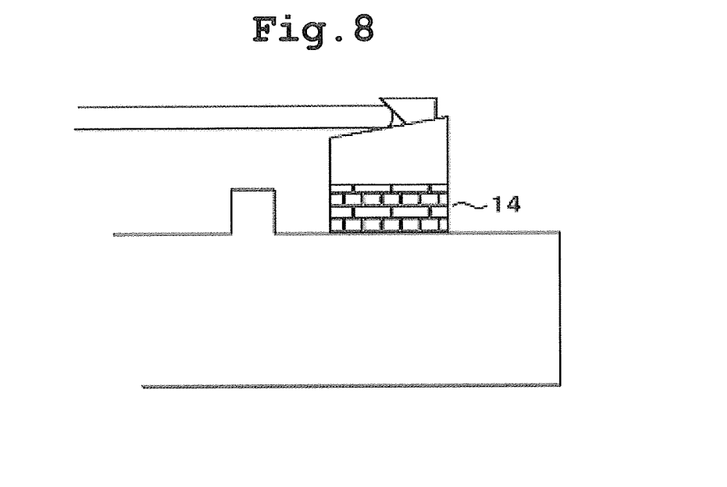
FIG. 8 shows the means for changing the height of the wafer holding means by use of the piezo element (a state where the piezo element is expanded).

A description is below given of a method for holding the outer circumference of the wafer 5 and further controlling the wafer 5 into a convex or concave shape. While the wafer 5 is rotated, the inspection apparatus or the like extracts data from the wafer 5. To counteract the centrifugal force resulting from the rotation of the wafer 5, the wafer 5 is held at its outer circumferential end face by an inclined wafer-receiving support 12 and a wafer holder 13 (although not detailed here, it is determined later). In this case, if the convex or concave shape of the flat surface close to the outer circumferential portion of the wafer 5 is controlled, it is necessary to change the position of the wafer-receiving support 12 in the thickness-direction of the wafer 5. An example of using the piezo element 14 is shown in FIGS. 7 and 8 as a method for realizing this structure in a compact manner. While the wafer 5 remains fixed, the convex and concave shape of the wafer 5 can be controlled. In addition, the flatness of the upper surface of the wafer 5 can be formed depending on situations.

A description is below given of another example of the means for forming the convex and concave shape of the wafer 5. The width of the groove and the width of each of the barriers on the both sides of the corresponding groove on the surface of the rotating table 4 are not described with FIG. 6.

Figure 9:
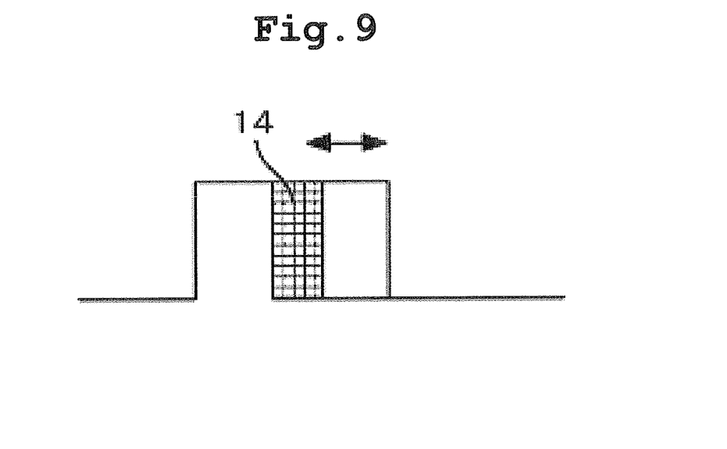
FIG. 9 shows means for changing the width of a barrier by use of the piezo element.

An example of changing the width of the barrier is shown in FIG. 9. When the width of the barrier is wide, pressure per unit area is the same as when the width is narrow. However, since the total force is increased due to the increased area, the wafer 5 can strongly be pushed up, which makes it possible to form the wafer 5 into a large convex shape. This structure is provided at a plurality of the grooves and of the convex portions arranged in the radial direction of the wafer. This makes it possible to form the convex and concave shapes of the wafer 5 by forces different in the radial direction. The formation of the flatness of the wafer 5 is facilitated; therefore it is possible to improve the accuracy of the flatness.

Further, the width of the concave portion between the barriers is made variable, which makes it possible to control the flat surface forming force of the wafer 5.

The above embodiment describes the method for adjusting the force pushing up the rear surface of the wafer 5 by controlling the pressure and flow of air and the method for controlling the flat surface forming force of the wafer 5 by making variable the width of the concave portion between the barriers. Another method conceivably involves regulating the temperature of air. If air temperature is increased, pressure rises. If air temperature is reduced, pressure lowers. A method for regulating air temperature is described below.

Air temperature may be controlled by controlling the supplied amount of air of two types, i.e., first air having first temperature and second air having second temperature which is higher than the first temperature. Alternatively, only the first air is supplied and a temperature control unit is installed in the passage for the first air to control the temperature of the first air.

Next, a description is below given of another example of the method for measuring the convex and concave shapes of the wafer 5.

Figure 10:
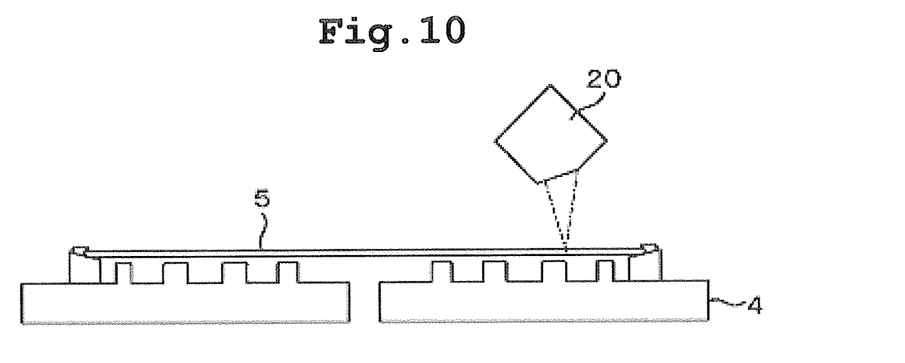
FIG. 10 shows means for measuring the flatness of a wafer by use of a laser displacement sensor.

The previous example is described in which the capacitance sensor is used as the displacement sensor. Other sensors can be applicable as the displacement sensor. For example, a method using a laser displacement sensor 20 shown in FIG. 10 can be applicable. Alternatively, if light reflected from the front surface of the wafer 5 is used, measurement light is emitted from above the upper surface of the wafer 5 and a phase between the measurement light and the light reflected from the front surface of the wafer 5 is measured. Thus, the position of the front surface of the wafer 5 can be measured by optical interferometry.

As with the displacement sensor mentioned earlier, a plurality of the interference measuring portions are installed in the radial direction of the wafer. This makes it possible to measure the entire surface of the wafer 5 while the wafer 5 is rotated. The interference method can provide a measurement resolution power of 0.25 nm.

The method using the variation of capacitance and the method using the phase variation due to optical interference are described as the method for measuring the surface of the wafer 5. If measuring methods are such that they are of a non-contact type, resolution performance is several nm and responsive frequency is several kHz, they satisfy the usage of the present embodiment. Thus, such measuring methods may be available.

The present embodiment describes the plurality of methods for controlling the shape of the substrate. Even if any of the methods is used, more advantageous effects than those of the conventional technologies can be produced. If a plurality of the methods are combined, a further excellent effect can be produced. Combinations of any methods are free in the scope of the technical concept disclosed in the present embodiment.

Also independently employing the technical concepts disclosed in the present embodiment is free in the scope of the disclosure of the present specification.

DESCRIPTION OF REFERENCE NUMERALS

1 Inspection apparatus
2 Inspecting section
3 Wafer holding device
4 Rotating table
5 Wafer
6 Wafer transfer robot
7 Cassette
8 Cassette table
9 Wafer holding means
10 Barrier
11 Displacement measurement sensor
12 Wafer-receiving support
13 Wafer holder
14 Piezo element
15 Elastic body
16 Flow controller
20 Laser displacement sensor

The invention claimed is:

1. An inspection apparatus for inspecting a substrate, comprising:
   a substrate mounting device,
   where the substrate mounting device is a rear surface non-contact type, and includes a holding portion disposed at an outer circumferential portion of the substrate mounting device so as to mount the substrate thereon;
   a structure, including a first piezo element, formed at a portion opposed to a rear surface of the substrate; and
   a first control section for controlling pressure between the rear surface of the substrate and the structure,
   where the first control section includes a second control section for controlling volume between the rear surface of the substrate and the structure.

2. The inspection apparatus according to claim 1, wherein the second control section includes a first drive section for driving the first piezo element.

3. An inspection apparatus for inspecting a substrate, comprising:
   a substrate mounting device,
   where the substrate mounting device is a rear surface non-contact type, and includes a holding portion disposed at an outer circumferential portion of the substrate mounting device so as to mount the substrate thereon;
   a structure formed at a portion opposed to a rear surface of the substrate;

first control section for controlling pressure between the rear surface of the substrate and the structure, where the holding section includes a second piezo element; and a second drive section for driving the second piezo element.

4. An inspection method for inspecting a substrate, comprising the steps of:

holding the substrate using a substrate mounting device which is a rear surface non-contact type;

controlling flatness of the substrate by controlling pressure on a rear surface side of the substrate; and inspecting the substrate, wherein a concavity-convexity forming structure is disposed on a portion opposed to the rear surface of the substrate, and the concavity-convexity forming structure includes a piezo element, and wherein volume between the rear surface of the substrate and the concavity-convexity forming structure is controlled.

5. The inspection apparatus according to claim 1, wherein the structure is concavity-convexity forming.

6. The inspection apparatus according to claim 1, wherein the structure is formed in a circle.

7. The inspection apparatus according to claim 1, wherein the structure is formed in a straight line.

8. The inspection apparatus according to claim 1, further comprising:

a first measuring section for measuring displacement of the substrate disposed on a side where the substrate is inspected;

wherein the first control section controls pressure between the rear surface of the substrate and the structure on the basis of a measurement result of the first measuring section.

9. The inspection apparatus according to claim 1, wherein the inspection apparatus includes a medium supply section for supplying a medium to a portion opposed to the rear surface of the substrate, and the first control section controls an amount of the medium.

10. The inspection apparatus according to claim 9, further comprising:

a second measuring section for measuring temperature of the medium; and wherein the control section controls the temperature of the medium on the basis of a measurement result of the second measuring section.

11. The inspection apparatus according to claim 2, wherein the holding section includes a second piezo element, and the inspection apparatus includes a second drive section for driving the second piezo element.

12. The inspection apparatus according to claim 3, wherein the structure is concavity-convexity forming.

13. The inspection apparatus according to claim 3, wherein the structure is formed in a circle.

14. The inspection apparatus according to claim 3, wherein the structure is formed in a straight line.

15. The inspection apparatus according to claim 3, further comprising:

a first measuring section for measuring displacement of the substrate disposed on a side where the substrate is inspected;

wherein the first control section controls pressure between the rear surface of the substrate and the structure on the basis of a measurement result of the first measuring section.

16. The inspection apparatus according to claim 15, wherein the substrate mounting device includes a medium supply section for supplying a medium to a portion opposed to the rear surface of the substrate, and the first control section controls an amount of the medium.

17. The inspection apparatus according to claim 3, further comprising:

a second measuring section for measuring temperature of the medium; and wherein the first control section controls the temperature of the medium on the basis of a measurement result of the second measuring section.

* * * * *